United States Patent
Ozminkowski, Jr.

(10) Patent No.: US 10,314,261 B2
(45) Date of Patent: Jun. 11, 2019

(54) HYBRID TOMATO VARIETY H1657

(71) Applicant: H.J. Heinz Company Brands LLC, Pittsburgh, PA (US)

(72) Inventor: Richard Henry Ozminkowski, Jr., Lodi, CA (US)

(73) Assignee: H.J. Heinz Company Brands LLC, Pittsburgh, PA (US)

( * ) Notice: Subject to any disclaimer, the term of this patent is extended or adjusted under 35 U.S.C. 154(b) by 0 days.

(21) Appl. No.: 15/856,290

(22) Filed: Dec. 28, 2017

(65) Prior Publication Data

US 2019/0053453 A1 Feb. 21, 2019

Related U.S. Application Data

(60) Provisional application No. 62/546,932, filed on Aug. 17, 2017.

(51) Int. Cl.
*A01H 5/10* (2018.01)
*A01H 5/08* (2018.01)

(52) U.S. Cl.
CPC ............. *A01H 5/08* (2013.01); *A01H 5/10* (2013.01)

(58) Field of Classification Search
None
See application file for complete search history.

(56) References Cited

U.S. PATENT DOCUMENTS 6,759,573 B2 * 7/2004 Olhoft ................. C12N 5/0025
435/419
7,939,728 B2 * 5/2011 Bunn ...................... A01H 5/08
435/411

* cited by examiner

*Primary Examiner* — Jason Deveau Rosen
(74) *Attorney, Agent, or Firm* — Fitch, Even, Tabin & Flannery LLP

(57) ABSTRACT

Hybrid tomato variety 'H1657' is described. The tomato variety is a ground-culture hybrid tomato variety suitable for machine harvest, and is adaptable to the climactic conditions of regions such as California (USA), Ontario (Canada), Australia, Portugal, Spain, and Italy.

23 Claims, 1 Drawing Sheet
(1 of 1 Drawing Sheet(s) Filed in Color)

HYBRID TOMATO VARIETY H1657

FIELD

This disclosure relates to the field of plant breeding. In particular, this disclosure relates to a new tomato (*Solanum lycopersicum*) variety denominated 'H1657'.

BACKGROUND

Breeding improved tomato varieties involves providing genetics that give an advantage to the grower, processor, consumer, or other members of the supply chain. The improvement may be in the form of field performance, disease resistance, factory performance, or a fruit quality characteristic. For a tomato variety to be suitable to be grown for processing, the variety must have a concentrated fruit setting and maturity, firm fruit, and sufficient rot tolerance to allow early fruit to remain rot-free while later fruit continues to develop and ripen.

Most commercial processing tomato varieties are hybrids resulting from a cross pollination of two true-breeding, inbred parents. Through the use of true-breeding lines, a hybrid is produced that often displays characteristics of each parent, and often demonstrates characteristics that are superior to either parent alone, or that allow a hybrid to mask inadequacies of the individual parents.

SUMMARY

Provided herein is a new and distinct tomato variety named 'H1657' that was developed to provide a ground-culture hybrid tomato variety that is suitable for machine harvest, and is adaptable to the climactic conditions of regions such as California (USA), Ontario (Canada), Australia, Portugal, Spain, and Italy.

The present disclosure provides the improved tomato variety 'H1657', which produces very good yields of very firm, medium-sized fruits, with a very high lycopene level resulting in exceptional, deep red color. The 'H1657' variety is resistant to *verticillium* wilt race 1, *fusarium* wilt races 1 and 2, and root knot nematode. Tolerance to fruit rot in 'H1657' is very good, allowing for once-over machine harvesting applications requiring extended field storage. Adaptability of 'H1657' is good, with commercially acceptable field performance when trialed in California (USA), Ontario (Canada), Portugal, Italy, Australia, and Spain. The fruit are acceptable for both peel and concentrated products.

In one embodiment, the present disclosure is directed to tomato seed designated as 'H1657' having ATCC Accession Number PTA-124673. In one aspect, the present disclosure is directed to a tomato plant, as well as any plant part or portion thereof isolated therefrom, produced by growing 'H1657' tomato seed. In another embodiment, the present disclosure is directed to a tomato plant and parts isolated therefrom having all the physiological, morphological and/or genetic characteristics of a tomato plant produced by growing 'H1657' tomato seed having ATCC Accession Number PTA-124673. In yet another aspect, the present disclosure is directed to a tomato plant having all of the characteristics of tomato variety 'H1657' listed in Table 1 below, wherein representative seed is deposited under ATCC Accession Number PTA-124673.

In another aspect, the present disclosure is directed to tomato seed having at least a first set of the chromosomes of tomato variety 'H1657', wherein representative seed is deposited under ATCC Accession Number PTA-124673. In still another aspect, the present disclosure is directed to an $F_1$ hybrid tomato seed, methods of making $F_1$ hybrid tomato seed, plants grown from the seed, leaf, ovule, pollen, rootstock, scion, fruit, cotyledon, embryo, meristem, anther, root, root tip, pistil, flower, stem, calli, stalk, hypocotyla, pericarp, or portion thereof isolated therefrom having 'H1657' as a parent, wherein 'H1657' is grown from 'H1657' tomato seed having ATCC Accession Number PTA-124673. The disclosure is also directed to a method of producing a tomato plant derived from tomato variety 'H1657', including crossing a plant of tomato variety 'H1657' with another tomato plant. The method may further comprise harvesting seed from the $F_1$ hybrid tomato seed and/or crossing the $F_1$ hybrid tomato plant with itself or another plant to produce seed from a progeny plant.

Tomato plant parts include leaf, ovule, pollen, cell, rootstock, scion, fruit, cotyledon, embryo, meristem, anther, root, root tip, pistil, flower, stem, calli, stalk, hypocotyl, pericarp, the like, and any portion thereof. In another embodiment, the present disclosure is further directed to tomato fruit, stem, leaf, root, root tip, pollen, cell, rootstock, scion, ovule, seed, and flower, and any portion thereof, isolated from 'H1657' tomato plants. In another aspect, the present disclosure is further directed to tissue culture of regenerable cells derived from 'H1657' tomato plants. The disclosure is further directed to a tomato plant regenerated from tissue culture. In another aspect, the disclosure is directed to a protoplast produced from tissue culture and a plant regenerated from the protoplast. At least in some approaches, the plant regenerated from the tissue culture or protoplast has all of the characteristics of tomato variety 'H1657' listed in Table 1.

In another aspect, the disclosure is directed to a method for producing a plant part, which at least in one aspect is tomato fruit, and harvesting the plant part. The disclosure also is directed to vegetatively propagating a plant of tomato variety 'H1657' by obtaining a part of the plant and regenerating a plant from the plant part. At least in some approaches, the regenerated plant has all of the characteristics of tomato variety 'H1657' listed in Table 1.

In yet another aspect, the present disclosure is further directed to a method of selecting tomato plants by a) growing 'H1657' tomato plants wherein the 'H1657' plants are grown from tomato seed having ATCC Accession Number PTA-124673; and b) selecting a plant from step a). In another embodiment, the present disclosure is further directed to tomato plants, plant parts and seeds produced by the tomato plants, where the tomato plants are isolated by the selection method.

In another aspect, the present disclosure is further directed to a method of breeding tomato plants by crossing a tomato plant with a plant grown from 'H1657' tomato seed having ATCC Accession Number PTA-124673. In another aspect, the tomato plant of tomato variety 'H1657' is self-pollinated. In still another aspect, the present disclosure is further directed to tomato plants, tomato parts from the tomato plants, and seeds produced therefrom where the tomato plant is isolated by the breeding method of the invention.

In another aspect, the disclosure relates to a plant of tomato variety 'H1657' comprising a transgene and/or a single locus conversion, and any seeds or plant parts isolated therefrom. The disclosure also relates to methods for preparing a plant of tomato variety 'H1657' comprising a transgene and/or a single locus conversion.

BRIEF DESCRIPTION OF THE DRAWING

The patent or application file contains at least one drawing executed in color. Copies of this patent or patent application publication with color drawings will be provided by the office upon request and payment of the necessary fee.

The FIGURE illustrates the fruit and plant of tomato variety 'H1657'.

DETAILED DESCRIPTION

Described herein is a new and distinct tomato variety named 'H1657' that was developed to provide a ground-culture hybrid tomato variety (i.e., not grown on stakes) that is suitable for machine harvest, and is adaptable to the climactic conditions of regions such as California (USA), Ontario (Canada), Australia, Portugal, Spain, and Italy.

Processing tomato quality parameters differ from those of fruit used in the fresh market. The processing characteristics are typically determined using a sample of hot-break tomato pulp or juice produced in a consistent manner to those familiar with the art. For example, a fixed mass of tomatoes may be cooked in a microwave oven for several minutes to halt any enzymatic breakdown of the sample, lost water is replaced, and the sample is pulped to remove skins and seed to produce a uniform juice sample. The juice sample can be analyzed for various quality parameters important to processing tomato including but not limited to gross viscosity measures such as juice Bostwick, soluble solids measures using a refractometer (°Brix), measures of acidity and pH, and measures of color (e.g. Hunter a/b score and levels of lycopene). The value of these traits depends on the product that is being commercially produced by the processing factory. In some instances, a factory will put a higher value on a thick viscosity variety, whereas in other instances, a thin viscosity will make a superior product and is preferred.

Processing tomato varieties combining resistance to *verticillium* wilt race 1 (*Verticillium dahlia*), *fusarium* wilt race 1 and 2 (*Fusarium oxysporum* pv. *lycopersici*), and root knot nematode (*Meloidogyne incognita*) are highly desirable in most climates around the world. Varieties with tolerance to ripe fruit rots (extended field storage) are also desirable because they are conducive to once-over machine harvesting, particularly in regions where rain can occur during harvest or there are delays in a harvesting schedule.

Moreover, in regions such as California, the industry has seen a considerable increase in pressure from two particular diseases: tomato spotted wilt virus (TSWV) and *Fusarium oxysporum* pv. *lycopersici* race 3 (*fusarium* wilt race 3). Thus, varieties with resistance to either or both are in high demand by both growers and processors to ensure a productive crop cycle.

Processing tomato varieties that can produce high yields under intense pressure from bacterial diseases such as bacterial canker (*Clavibacter michiganensis* subsp. *michiganensis*) and bacterial spot, caused by various *Xanthomonas* species, are highly desirable in humid tomato production regions around the world, such as Ohio, Michigan, and Brazil.

Moreover, an additional important contribution that tomatoes provide to the human diet is the antioxidant lycopene. Specifically, processed tomato products are the primary source of tomato intake in the US diet and other countries around the world. Higher levels of lycopene are beneficial both from a nutritional standpoint and from a consumer perception and quality standpoint. Tomato varieties having higher levels of lycopene result in products with a deeper red color that can be considered an indicator of higher product quality. Thus, a tomato variety with a higher level of lycopene and improved color in general can be valuable from a nutritional standpoint, a quality standpoint, and desirability by the consumer. However, to be commercially viable, the tomato variety must perform acceptably in the field and factory as required by any other processing tomato variety. Often, varieties with enhanced lycopene suffer agronomic defects in yield, fruit firmness, or field storage.

Hybrid Tomato Variety 'H1657'

Tomato plants of 'H1657' are resistant to *verticillium* wilt race 1, *fusarium* wilt races 1 and 2, and southern root knot nematode. Plants and immature fruit are darker green in color than typical commercial varieties. Plants grow in a medium, sprawling habit as compared to tomato varieties of the same market class. Fruit of 'H1657' are medium (73 gram), and blocky/square in shape with a thick pericarp. While the external color of the fruit is slightly orange, the internal color is very intensely red, which is among the variety's most notable and desirable qualities. Fruit are also considered to have an extended field storage which delays the onset of fruit rots after reaching red-ripe maturity.

Stability of the Variety 'H1657'

Variety 'H1657' is uniform and stable within commercially acceptable limits. As is true with other tomato varieties, a small percentage of variants can occur within commercially acceptable limits for almost any characteristic during the course of repeated multiplication. However, no variants were observed during the two years in which the variety was observed to be uniform and stable.

Hybrid tomato variety 'H1657' has the following physiological, morphological, and other characteristics as set forth in Tables 1-4 below.

TABLE 1

Characterization of tomato variety 'H1657' compared to two industry standards, 'H5608' and 'H1311'.

| Character | Variety 'H1657' | Check Variety 1 'H5608' | Check Variety 2 'H1311' |
|---|---|---|---|
| Seedling | | | |
| Anthocyanin in hypocotyl: | Present | Present | Present |
| Habit of 3-4 week seedling: | Normal | Normal | Normal |
| Mature Plant | | | |
| Height: | 36 | 44 | 34 |
| Growth Type: | Determinate | Determinate | Determinate |
| Form: | Normal | Sprawling | Normal |

TABLE 1-continued

Characterization of tomato variety 'H1657' compared to two industry standards, 'H5608' and 'H1311'

| Character | Variety 'H1657' | Check Variety 1 'H5608' | Check Variety 2 'H1311' |
|---|---|---|---|
| Size of Canopy: | Medium | Large | Medium |
| Habit: | Sprawling | Sprawling | Sprawling |
| Stem | | | |
| Branching: | Profuse | Profuse | Profuse |
| Branching at Cotyledon: | Absent | Absent | Absent |
| Number of nodes below first inflorescence: | 4-7 nodes | 4-7 nodes | 4-7 nodes |
| Number of nodes between early inflorescence: ($1^{st}$-$2^{nd}$, $2^{nd}$-$3^{rd}$): | 1-2 nodes | 1-2 nodes | 1-2 nodes |
| # nodes between later inflorescence: | 1-2 nodes | 1-2 nodes | 1-2 nodes |
| Pubescence on younger stems: | Sparse | Sparse | Sparse |
| Leaf | | | |
| Type: | Tomato | Tomato | Tomato |
| Morphology: | Compound with major and minor leaflets (FIG. 3) | Compound with major and minor leaflets | Compound with major and minor leaflets |
| Margins of Major Leaflets: | Shallowly Toothed | Nearly entire | Shallowly Toothed |
| Marginal Rolling or Wiltiness: | Moderate | Moderate | Moderate |
| Onset of Leaflet Rolling: | Midseason | Midseason | Midseason |
| Surface of Major Leaflets: | Rugose | Rugose | Rugose |
| Pubescence: | Normal | Normal | Normal |
| Inflorescence | | | |
| Type: | Forked | Forked | Forked |
| Number of flowers in inflorescence average: | 6 | 5 | 6 |
| Leafy or "running" inflorescence: | Absent | Absent | Absent |
| Flower | | | |
| Calyx: | Normal | Normal | Normal |
| Calyx-Lobes: | Shorter than corolla 1 | Shorter than corolla | Shorter than corolla |
| Corolla Color: | Gold | Yellow | Gold |
| Style pubescence: | Sparse | Sparse | Sparse |
| Anthers: | Fused/Tubed | Fused/Tubed | Fused/Tubed |
| Fasciation: | Absent | Absent | Absent |
| 1st flower of 2nd or 3rd Inflorescence: | Absent | Absent | Absent |
| Fruit | | | |
| Typical shape in longitudinal section: | Blocky | Blocky oval | Blocky oval |
| Shape of transverse section: | Round | Round | Round |
| Shape of stem end: | Indented | Indented | Indented |
| Shape of blossom end: | Flat | Flat | Flat |
| Shape of pistil scar: | Dot | Dot | Dot |
| Abscission layer: | Absent | Absent | Absent |
| Point of detachment fruit at harvest: | At calyx | At calyx | At calyx |
| Length of pedicel (joint to calyx attachment) (cm): | n/a | n/a | n/a |
| Length of mature fruit (cm) (stem axis) (cm): | 5.8 | 5.2 | 6.3 |
| Diameter of fruit at widest point (cm): | 4.5 | 3.8 | 4.4 |
| Weight of mature fruit (g): | 73 | 75 | 72 |
| Number of locules: | 2-4 | 2-4 | 2-4 |
| Fruit surface: | Smooth | Smooth | Smooth |
| Fruit base color (mature green stage): | Medium green | Yellow green | Medium green |
| Fruit pattern (mature green stage): | Uniform | Uniform | Uniform |
| Shoulder color if different from base: | n/a | n/a | n/a |
| Fruit color full ripe: | Red | Red | Red |
| Flesh color full ripe: | Red | Red | Red |
| Flesh color: | Uniform | Uniform | Uniform |
| Locular gel color of table-ripe fruit | Red | Yellow | Red |
| Ripening: | Uniform | Uniform | Uniform |

TABLE 1-continued

Characterization of tomato variety 'H1657' compared to two industry standards, 'H5608' and 'H1311'

| Character | Variety 'H1657' | Check Variety 1 'H5608' | Check Variety 2 'H1311' |
|---|---|---|---|
| Ripening: | Uniformly | Uniformly | Uniformly |
| Stem scar size: | Small | Small | Small |
| Core: | Present | Coreless | Present |
| Epidermis color: | Yellow | Yellow | Yellow |
| Epidermis: | Normal | Normal | Normal |
| Epidermis texture: | Average | Tough | Average |
| Thickness or pericarp (mm): | 6 | 8 | 6 |
| Resistance to fruit disorder: | Not tested | Not tested | Not tested |
| Disease and Pest Reactions Viral Diseases | | | |
| Cucumber Mosaic: | n/t | n/t | n/t |
| Curly Top: | n/t | n/t | n/t |
| Potato-y Virus: | n/t | n/t | n/t |
| Blotch Ripening: | n/t | n/t | n/t |
| Tobacco Mosaic Race 0: | n/t | n/t | n/t |
| Tobacco Mosaic Race 1: | n/t | n/t | n/t |
| Tobacco Mosaic Race 2: | n/t | n/t | n/t |
| Cracking, Concentric: | n/t | n/t | n/t |
| Tobacco Mosaic Race $2^2$: | n/t | n/t | n/t |
| Tomato Spotted Wilt: | Susceptible | Resistant | Susceptible |
| Tomato Yellows: | n/t | n/t | n/t |
| Gold Fleck: | n/t | n/t | n/t |
| Others: | n/t | n/t | n/t |
| Bacterial Disease | | | |
| Bacterial Canker (*Clavibacter michiganense*): | Susceptible | Susceptible | Susceptible |
| Bacterial Soft Rot (*Erwinia carotovora*): | n/t | n/t | n/t |
| Bacteria Speck (*Pseudomonas tomato*): | Susceptible | Resistant | Susceptible |
| Bacterial Spot (*Xanthomonas* spp.): | Susceptible | Susceptible | Susceptible |
| Bacterial Wilt (*Ralstonia solanacearum*): | n/t | n/t | n/t |
| Other Bacterial Disease: | n/t | n/t | n/t |
| Fungal Disease | | | |
| Anthracnose (*Colletotrichum* spp.): | n/t | Susceptible | n/t |
| Brown Root Rot or Corky Root (*Pyrenochaeta lycopersici*): | n/t | Susceptible | n/t |
| Collar Rot or Stem Canker (*Alternaria solani*): | n/t | Susceptible | n/t |
| Early Blight Defoliation (*Alternaria solani*): | Susceptible | Susceptible | Susceptible |
| *Fusarium* Wilt Race 1 (*F. oxysporum f. lycopersici*): | Resistant | Resistant | Resistant |
| *Fusarium* Wilt Race 2 (*F. oxysporum f. lycopersici*): | Resistant | Resistant | Resistant |
| *Fusarium* Wilt Race 3 (*F. oxysporum f. lycopersici*): | Susceptible | Susceptible | Susceptible |
| Grey Leaf Spot (*Stemphylium* spp.): | n/t | n/t | n/t |
| Late Blight, race 0 (*Phytophthora infestans*): | Susceptible | Susceptible | Susceptible |
| Late Blight, race 1 (*Phytophthora infestans*): | n/t | n/t | n/t |
| Leaf Mold race 1 (*Cladosporium fulvum*): | n/t | n/t | n/t |
| Leaf Mold race 2 (*Cladosporium fulvum*): | n/t | n/t | n/t |
| Leaf Mold race 3 (*Cladosporium fulvum*): | n/t | n/t | n/t |
| Leaf Mold Other Races: | n/t | n/t | n/t |
| Nailhead Spot (*Alternaria tomato*): | n/t | n/t | n/t |
| Seporia Leaf spot (*S. lycopersici*): | n/t | n/t | n/t |
| Target Leaf spot (*Corynespora cassiicola*): | n/t | n/t | n/t |
| *Verticillium* Wilt Race 1 (*V. dahliae* race 1): | Resistant | Resistant | Resistant |
| *Verticillium* Wilt Race 2 (*V. dahliae* race 2): | n/t | Susceptible | n/t |
| Other Fungal Disease: | n/t | n/t | n/t |

TABLE 1-continued

Characterization of tomato variety 'H1657' compared to two industry standards, 'H5608' and 'H1311'

| Character | Variety 'H1657' | Check Variety 1 'H5608' | Check Variety 2 'H1311' |
|---|---|---|---|
| Insects and Pests | | | |
| Colorado Potato Beetle (*L. decemlineata*): | n/t | n/t | n/t |
| Root Knot Nematode (*M.* sp.): | Resistant | Resistant | Resistant |
| Spider Mites (*Tetranychus* spp.): | n/t | n/t | n/t |
| Sugar Beet Army Worm (*S. exigua*): | n/t | n/t | n/t |
| Tobacco Flea Beetle (*E. hiritipennis*): | n/t | n/t | n/t |
| Tomato Hornworm (*M. quinquemaculata*): | n/t | n/t | n/t |
| Tomato Fruit worm (*H. zea*): | n/t | n/t | n/t |
| Whitefly (*T. vaporariorum*): | n/t | n/t | n/t |
| Other: | n/t | n/t | n/t |

Chemistry and Composition of Full-Ripe Fruits

TABLE 2

Hot-break tomato juice characteristics for new variety 'H1657' and two check varieties 'H5608' and 'H1311'

| | Variety 'H1657' | Check Variety 1 'H5608' | Check Variety 2 'H1311' |
|---|---|---|---|
| Serum viscosity (centistokes) | 9.4 | 10.4 | 10.3 |
| Juice Bostwick (cm) | 11.9 | 10.8 | 10.9 |
| Soluble solids (°Brix) | 5.0 | 5.0 | 4.9 |
| Lycopene (ppm) | 183 ppm | 133 ppm | 196 ppm |
| Hunter a/b (1 year data) | 2.30 | 2.28 | 2.34 |

Average of 2 years of trials in California in a total of 28 locations in 2014 and 2015.

TABLE 3

Phenology

| | Variety 'H1657' | Check Variety 1 'H5608' | Check Variety 2 'H1311' |
|---|---|---|---|
| Fruiting Season | Short | Short | Short |
| Relative Maturity | Medium Late | Late | Late |

TABLE 4

Adaptation

| | Variety 'H1657' | Check Variety 1 'H5608' | Check Variety 2 'H1311' |
|---|---|---|---|
| Culture | Field | Field | Field |
| Principle use | Concentrated | Concentrated, Whole-pack, | Concentrated Whole-pack, |
| Machine harvest | Yes | Yes | Yes |
| Regions of adaptability | | | |
| California Sacramento/upper San Joaquin valley | Yes 2 | Yes 2 | Yes 1 |
| California lower SJ valley | Yes 1 | Yes 1 | Yes 2 |
| Northeastern USA | Yes 3 | No | No |

If more than one category applies, they are listed in rank order.

Comparison of 'H1657' to Closest Varieties

Data in Tables 1, 3, and 4 are based primarily upon trials conducted in Collegeville, Calif. from two replications, non-staked, in a research plot environment. Comparisons among varieties for processing traits (Table 2) were done over two years of side-by side testing throughout California. Disease resistance and adaptability assessments are based upon numerous observations collected throughout California, in inoculated pathology experiments, with DNA marker associations, and in field tests in climates with specific disease pressure for ripe fruit rots, bacterial spot, bacterial canker, and early blight, and late blight, including Ontario, Canada.

Several characteristics can distinguish 'H1657' from other commercial processing tomato varieties, including 'H5608'. In particular, the intense internal red fruit color and dark foliage of 'H1657' is more pronounced than most varieties. Another characteristic that distinguishes 'H1657' from 'H5608' is that 'H1657' is susceptible to TSWV and its foliage is less vigorous. Processing characteristics of 'H1657' are similar to 'H5608'. Furthermore, 'H1657' shows a wider adaptation to humid climates and has better resistance to ripe fruit rots than 'H5608'. 'H1311' is a recent variety introduction (described in U.S. Pub. No. 2015-0327457) that also has a very high level of lycopene. 'H1657' is distinguished from 'H1311' by having superior field performance (including foliage health), blockier fruit shape, better resistance to fruit rots, and a slightly less intense internal red fruit color.

Further Embodiments

Additional methods include, without limitation, chasing selfs. Chasing selfs involves identifying inbred plants among tomato plants that have been grown from hybrid tomato seed. Once the seed is planted, the inbred plants may be identified and selected due to their decreased vigor relative to the hybrid plants that grow from the hybrid seed. By locating the inbred plants, isolating them from the rest of the plants, and self-pollinating them (i.e., "chasing selfs"), a breeder can obtain an inbred line that is identical to an inbred parent used to produce the hybrid. Accordingly, another aspect of the disclosure relates a method for producing an inbred tomato variety by: planting seed of the tomato variety 'H1657'; growing plants from the seed; identifying one or more inbred tomato plants; controlling pollination in a manner which preserves homozygosity of the one or more inbred plants; and harvesting resultant seed from the one or more inbred plants. The step of identifying the one or more inbred tomato plants may further include identifying plants with decreased vigor, i.e., plants that appear less robust than plants of the tomato variety 'H1657'. Tomato plants capable of expressing substantially all of the physiological and morphological characteristics of the parental inbred lines of tomato variety 'H1657' include tomato plants obtained by chasing selfs from seed of tomato variety 'H1657'.

One of ordinary skill in the art will recognize that once a breeder has obtained inbred tomato plants by chasing selfs from seed of tomato variety 'H1657', the breeder can then produce new inbred plants such as by sib-pollinating, or by crossing one of the identified inbred tomato plant with a plant of the tomato variety 'H1657'.

The disclosure further includes introducing one or more desired traits into the tomato variety 'H1657'. For example, the desired trait may include male sterility, male fertility, herbicide resistance, insect resistance, disease resistance, and drought resistance.

The desired trait may be found on a single gene or combination of genes. The desired trait may be a genetic locus that is a dominant or recessive allele. The genetic locus may be a naturally occurring tomato gene introduced into the genome of a parent of the variety by backcrossing, a natural or induced mutation, or a transgene introduced through genetic transformation techniques. For a genetic locus introduced through transformation, the genetic locus may comprise one or more transgenes integrated at a single chromosomal location. Accordingly, the disclosure provides tomato plants or parts thereof that have been transformed with one or more transgenes (i.e., a genetic locus comprising a sequence introduced into the genome of a tomato plant by transformation) to provide a desired trait. In one aspect, the one or more transgenes are operably linked to at least one regulatory element.

The gene(s) may be introduced to tomato variety 'H1657' through a variety of well-known techniques, including for example, molecular biological, other genetic engineering, or plant breeding techniques, such as recurrent selection, backcrossing, pedigree breeding, molecular marker (Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs) (also referred to as Microsatellites)), enhanced selection, genetic marker enhanced selection, and transformation. Accordingly, tomato seed, plants, and parts thereof produced by such genetic engineering or plant breed techniques are also part of the present disclosure.

Also provided herein are single locus converted plants and seeds developed by backcrossing wherein essentially all of the morphological and physiological characteristics of an inbred are recovered in addition to the characteristics conferred by the single locus transferred into the inbred via the backcrossing technique. A single locus may comprise one gene, or in the case of transgenic plants, one or more transgenes integrated into the host genome at a single site (locus). One or more locus conversion traits may be introduced into a single tomato variety.

DEPOSIT INFORMATION

A deposit of tomato variety 'H1657' is maintained by HeinzSeed Company, having an address at 6755 CE Dixon St, Stockton, Calif. 95206, United States of America. Access to this deposit will be available during the pendency of this application to persons determined by the Commissioner of Patents and Trademarks to be entitled thereto under 37 C.F.R. § 1.14 and 35 U.S.C. § 122.

At least 2,500 seeds of tomato variety 'H1657' were deposited on Dec. 12, 2017 according to the Budapest Treaty in the American Type Culture Collection (ATCC), P.O. Box 1549, MANASSAS, Va. 20108 USA. The deposit has been assigned ATCC number PTA-124673. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed for the enforceable life of the patent.

The deposit will be maintained in the ATCC depository, which is a public depository, for a period of 30 years, or 5 years after the most recent request, or for the effective life of the patent, whichever is longer, and will be replaced if the deposit becomes nonviable during that period.

What is claimed is:

1. Tomato seed designated as 'H1657', representative sample of seed having been deposited under ATCC Accession Number PM PTA-124673.

2. A plant produced by growing the seed of claim 1.

3. A plant part from the plant of claim 2, wherein the plant part comprises at least one cell from tomato variety 'H1657'.

4. The plant part of claim 3, wherein the part is selected from the group consisting of leaf, ovule, pollen, cell, rootstock, scion, fruit, cotyledon, meristem, anther, root, root tip, pistil, flower, stem, calli, stalk, hypocotyl, pericarp, and portion thereof.

5. A tomato plant having all the physiological and morphological characteristics of the tomato plant of claim 2.

6. A plant part from the plant of claim 5, wherein the plant part comprises at least one cell from tomato variety 'H1657'.

7. The plant part of claim 6, wherein the part is selected from the group consisting of leaf, ovule, pollen, cell, rootstock, scion, fruit, cotyledon, meristem, anther, root, root tip, pistil, flower, stem, calli, stalk, hypocotyl, pericarp, and portion thereof.

8. A tomato plant having all the physiological and morphological characteristics of tomato variety 'H1657', wherein a representative sample of seed has been deposited under ATCC Accession Number PTA-124673.

9. A plant part from the plant of claim 8, wherein the plant part comprises at least one cell from tomato variety 'H1657'.

10. The plant part of claim 9, wherein the part is selected from the group consisting of leaf, ovule, pollen, cell, rootstock, scion, fruit, cotyledon, meristem, anther, root, root tip, pistil, flower, stem, calli, stalk, hypocotyl, pericarp, and portion thereof.

11. Pollen of the plant of claim 2.

12. An ovule of the plant of claim 2.

13. A tissue culture of regenerable cells from a plant part of claim 3, wherein said tissue culture comprises at least one cell of tomato variety 'H1657'.

14. A tomato plant regenerated from the tissue culture of claim 13, the plant having all the physiological and morphological characteristics of tomato variety 'H1657', wherein a representative sample of seed has been deposited under ATCC Accession Number PTA-124673.

15. A protoplast produced from the tissue culture of claim 13, wherein a plant regenerated from the protoplast has all the physiological and morphological characteristics of tomato variety 'H1657'.

16. A method of producing a tomato plant derived from tomato variety 'H1657', the method comprising crossing the plant of claim 2 with another tomato plant to produce a $F_1$ hybrid tomato plant.

17. The method of claim 16, further comprising harvesting seed from the $F_1$ hybrid tomato plant.

18. The method of claim 16, further comprising crossing the $F_1$ hybrid tomato plant with itself or another plant to produce seed from a progeny plant.

19. The plant of claim 2, said plant having all the physiological and morphological characteristics of tomato variety 'H1657', further comprising a transgene.

20. The plant of claim 2, said plant having all the physiological and morphological characteristics of tomato variety 'H1657', further comprising a single locus conversion.

21. A method for producing a tomato fruit, the method comprising:
    growing the tomato plant of claim 2 to produce a tomato fruit; and
    harvesting the tomato fruit.

22. A method for producing a tomato seed comprising:
    self-pollinating the tomato plant of claim 2; and
    harvesting the resultant tomato seed.

23. A method of vegetatively propagating the plant of claim 2, the method comprising:
    obtaining a part of the plant; and
    regenerating a plant from the part, the regenerated plant having all the physiological and morphological characteristics of tomato variety 'H1657'.

* * * * *

UNITED STATES PATENT AND TRADEMARK OFFICE
CERTIFICATE OF CORRECTION

PATENT NO. : 10,314,261 B2
APPLICATION NO. : 15/856290
DATED : June 11, 2019
INVENTOR(S) : Richard Henry Ozminkowski, Jr.

Page 1 of 1

It is certified that error appears in the above-identified patent and that said Letters Patent is hereby corrected as shown below:

In the Claims

Column 12, Line 28, in Claim 1, after "Number" delete "PM".

Signed and Sealed this
Seventh Day of April, 2020

Andrei Iancu
*Director of the United States Patent and Trademark Office*